(12) United States Patent  
Kunimoto

(10) Patent No.: US 9,977,138 B2  
(45) Date of Patent: May 22, 2018

(54) THERMAL NEUTRON DETECTING DEVICE, SCINTILLATOR UNIT, AND THERMAL NEUTRON DETECTING SYSTEM

(71) Applicant: YASU MEDICAL IMAGING TECHNOLOGY CO., LTD., Yasu-shi (JP)

(72) Inventor: Fumiaki Kunimoto, Shiga (JP)

(73) Assignee: YASU MEDICAL IMAGING TECHNOLOGY CO., LTD., Yasu-shi (JP)

( * ) Notice: Subject to any disclaimer, the term of this patent is extended or adjusted under 35 U.S.C. 154(b) by 0 days. days.

(21) Appl. No.: 15/531,655

(22) PCT Filed: Sep. 9, 2015

(86) PCT No.: PCT/JP2015/075631  
§ 371 (c)(1),  
(2) Date: May 30, 2017

(87) PCT Pub. No.: WO2017/042916  
PCT Pub. Date: Mar. 16, 2017

(65) Prior Publication Data  
US 2017/0329028 A1 Nov. 16, 2017

(51) Int. Cl.  
*G01F 1/00* (2006.01)  
*G01T 3/06* (2006.01)  
*A61N 5/10* (2006.01)

(52) U.S. Cl.  
CPC .............. *G01T 3/06* (2013.01); *A61N 5/1075* (2013.01); *A61N 2005/109* (2013.01)

(58) Field of Classification Search  
CPC .. G01T 3/06; G01T 1/203; G01T 3/00; G01T 1/2018

(Continued)

(56) References Cited

U.S. PATENT DOCUMENTS 8,963,094 B2 * 2/2015 Gozani .................. G01T 1/203  
                                                250/363.02  
9,103,921 B2 * 8/2015 Torres ................... G01T 1/2002  
(Continued)

FOREIGN PATENT DOCUMENTS

JP    2006-526791 A    11/2006  
JP    2014-190754 A    10/2014  
(Continued)

OTHER PUBLICATIONS

International Search Report dated Dec. 15, 2015 in PCT/JP2015/075631 filed Sep. 9, 2015.

(Continued)

*Primary Examiner* — Taeho Jo  
(74) *Attorney, Agent, or Firm* — Oblon, McClelland, Maier & Neustadt, L.L.P.

(57) ABSTRACT

A thermal neutron detecting device comprises a scintillator unit including a scintillator layer and a nuclear capture reaction layer, and an optical sensor array unit. The scintillator layer emits light upon receiving incident gamma ray or charged particles. The nuclear capture reaction layer is laminated on a side of the scintillator layer on which the gamma ray or the charged particles are incident, and includes first cell regions and second cell regions two-dimensionally, dispersedly arranged along an incidence plane of the gamma ray or the charged particles. The first cell regions contain a $^6$Li compound as a nuclear capture reaction material yielding nuclear capture reaction with incident thermal neutrons to generate the charged particles. The second cell regions contain no nuclear capture reaction material. The optical sensor array unit is capable of detecting a quantity of the emitted light in association with each of the first and second cell regions.

14 Claims, 12 Drawing Sheets

(58) Field of Classification Search
USPC .................................................. 250/361 R
See application file for complete search history.

(56) References Cited

U.S. PATENT DOCUMENTS

| | | | | |
|---|---|---|---|---|
| 9,274,237 | B2* | 3/2016 | Zaitseva | G21K 4/00 |
| 9,678,225 | B1* | 6/2017 | Feng | G01T 1/208 |
| 2005/0023479 | A1 | 2/2005 | Grodzins | |
| 2006/0138340 | A1* | 6/2006 | Ianakiev | G01T 3/008 |
| | | | | 250/390.01 |
| 2008/0191140 | A1* | 8/2008 | McDevitt | G01T 1/202 |
| | | | | 250/390.11 |
| 2009/0045348 | A1* | 2/2009 | Stuenkel | G01T 3/06 |
| | | | | 250/390.11 |
| 2009/0166549 | A1* | 7/2009 | Czirr | G01T 3/06 |
| | | | | 250/390.07 |
| 2011/0049379 | A1* | 3/2011 | Moses | G01T 3/08 |
| | | | | 250/390.01 |
| 2011/0233420 | A1* | 9/2011 | Feller | G01T 3/00 |
| | | | | 250/391 |
| 2011/0291014 | A1* | 12/2011 | Kusner | G01T 1/20 |
| | | | | 250/362 |
| 2012/0280132 | A1* | 11/2012 | Nakamura | G01T 1/20 |
| | | | | 250/368 |
| 2013/0168560 | A1* | 7/2013 | Yang | G01T 3/06 |
| | | | | 250/366 |
| 2013/0341519 | A1* | 12/2013 | Li | G01T 3/06 |
| | | | | 250/368 |
| 2014/0042330 | A1* | 2/2014 | Gozani | G01T 1/203 |
| | | | | 250/367 |
| 2014/0077088 | A1* | 3/2014 | Feller | G01T 3/00 |
| | | | | 250/370.05 |
| 2014/0077089 | A1* | 3/2014 | Orava | G01T 3/08 |
| | | | | 250/370.05 |
| 2014/0224992 | A1* | 8/2014 | Kusner | G01T 1/20 |
| | | | | 250/361 R |
| 2014/0299781 | A1* | 10/2014 | Hultman | C23C 14/0635 |
| | | | | 250/390.01 |
| 2014/0339433 | A1* | 11/2014 | Feller | G01T 3/00 |
| | | | | 250/370.05 |
| 2014/0374606 | A1* | 12/2014 | Gendotti | G01T 3/06 |
| | | | | 250/361 R |
| 2015/0241579 | A1* | 8/2015 | Menge | G01V 5/0091 |
| | | | | 250/368 |
| 2016/0018538 | A1* | 1/2016 | Bendahan | G01T 3/008 |
| | | | | 250/390.01 |
| 2016/0091618 | A1* | 3/2016 | Gozani | G01T 1/203 |
| | | | | 250/367 |
| 2016/0259070 | A1* | 9/2016 | Fukuda | G01T 3/06 |
| 2016/0266262 | A1* | 9/2016 | Fukuda | G01T 3/06 |
| 2017/0052265 | A1* | 2/2017 | Fukuda | G01T 1/20 |
| 2017/0184730 | A1* | 6/2017 | Zygmanski | G01T 1/208 |

FOREIGN PATENT DOCUMENTS

| | | |
|---|---|---|
| JP | 2015-111107 A | 6/2015 |
| WO | WO 2005/008287 A1 | 1/2005 |

OTHER PUBLICATIONS

Notification of Reason for Refusal dated May 31, 2016 in Japanese Patent Application No. 2016-523337 (with English language translation).

Notification of Reason for Refusal dated Aug. 2, 2016 in Japanese Patent Application No. 2016-523337 (with English language translation).

Decision to Grant a Patent dated Aug. 23, 2016 in Japanese Patent Application No. 2016-523337 (with English language translation).

Masayori Ishikawa, et al., "Development of Real-time Thermal Neutron Monitor for Boron Neutron Capture Therapy", Journal of Radiation Research, vol. 31, No. 4, 2005, pp. 279-285.

* cited by examiner

EXAMPLES) X=10 TO 30cm
Y=10 TO 30cm
a=2.5mm TO 1cm
b=2.5mm TO 1cm

EXAMPLES) PE=2cm or <100 $\mu$m
S=50 TO 300 $\mu$m
L=10 TO 50 $\mu$m

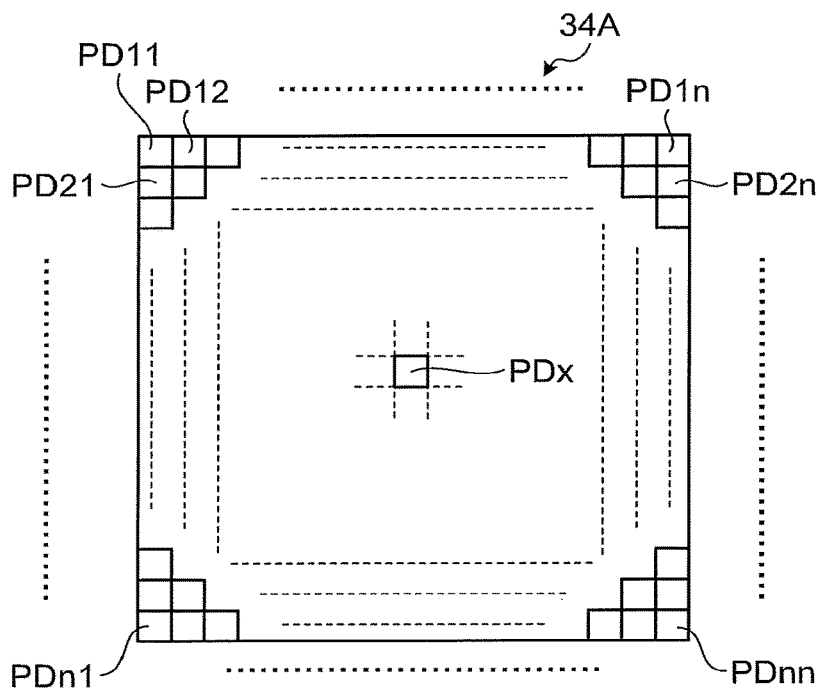
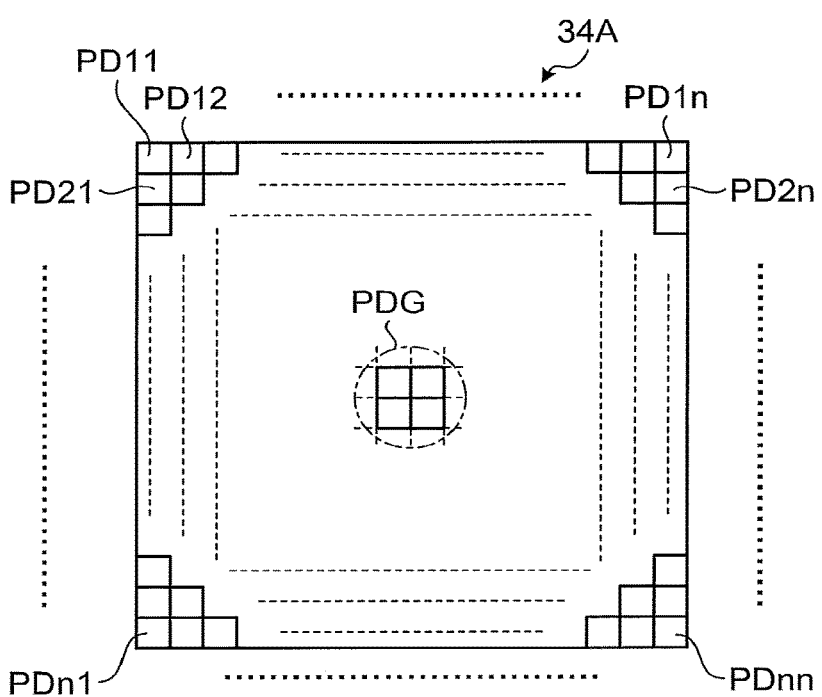

EXAMPLES) X=10 TO 30cm
Y=10 TO 30cm
a=2.5mm TO 1cm
b=2.5mm TO 1cm

EXAMPLES) PE=2cm or <100 μm

S1=50 TO 300 μm

EXAMPLES) S=50 TO 300 μm

EXAMPLES) S1=50 TO 300 μm

THERMAL NEUTRON DETECTING DEVICE, SCINTILLATOR UNIT, AND THERMAL NEUTRON DETECTING SYSTEM

CROSS-REFERENCE TO RELATED APPLICATIONS

This application is national stage application of International Application No. PCT/JP2015/075631, filed Sep. 9, 2015, which designates the United States, incorporated herein by reference.

FIELD

Embodiments of the present invention relate to a thermal neutron detecting device, a scintillator unit, and a thermal neutron detecting system.

BACKGROUND

Conventionally, therapy for selectively destroying only tumor cells has been known, such as boron neutron capture therapy (BNCT) using nuclear reaction between boron ($^{10}B$) and low-energy neutrons.

Neutrons are roughly classified, for example, into the following categories based on energy (speed) although different categories are applied depending on fields of study.

| | |
|---|---|
| Thermal neutron | (to 0.5 eV) |
| Epithermal neutron | (0.5 eV to 10 keV) |
| Fast neutron | (10 keV to 20 MeV) |

The thermal neutrons and the epithermal neutrons are used for the above-mentioned boron neutron capture therapy.

CITATION LIST

Patent Literature

Patent Literature 1: Japanese Patent Application Laid-open No. 2014-190754

Non Patent Literature 1: Masayori ISHIKAWA and 5 others, "Development of Real-time Thermal Neutron Monitor for Boron Neutron Capture Therapy", Journal of Radiation Research, Vol. 31 (2005), No. 4, pp. 279 to 285

SUMMARY

Technical Problem

The thermal neutrons are low-energy particles in thermal equilibrium with surroundings, having average speed of 2,200 m/sec and energy of approximately 0.025 eV at normal temperature of 300 K, and they are non-charged particles. It is therefore difficult to detect the thermal neutrons.

In general, neutrons are detected by a secondary particle detecting method in which secondary charged particles along with nuclear reaction or recoil charged particles converted from neutrons are detected. For a therapeutic method, however, more accurate detection of a neutron irradiance (intensity value of a neutron flux) is desired.

The present invention has been made in view of the above situations and an object thereof is to provide a thermal neutron detecting device, a scintillator unit, and a thermal neutron detecting system capable of accurately detecting the thermal neutron irradiance (neutron flux: the number of neutrons passing through a unit area per unit time) on a two-dimensional plane.

Solution to Problem

A scintillator unit of a thermal neutron detecting device according to an embodiment includes a scintillator layer that emits light upon receiving incident gamma ray or charged particles, and a nuclear capture reaction layer laminated on a side of the scintillator layer on which the gamma ray or the charged particles are incident, and including first cell regions and second cell regions two-dimensionally, dispersedly arranged along an incidence plane of the gamma ray or the charged particles, the first cell regions containing a $^{6}Li$ compound as a nuclear capture reaction material that yields nuclear capture reaction with incident thermal neutrons to generate the charged particles, the second cell regions containing no nuclear capture reaction material.

An optical sensor array unit is disposed at the scintillator layer side of the scintillator unit and can detect a quantity of the emitted light in association with each of the first and second cell regions.

BRIEF DESCRIPTION OF DRAWINGS

FIG. 7 is a view for explaining an example of output of the scintillator plate corresponding to the cell region.

FIG. 8 is a view for explaining another example of the output of the scintillator plate corresponding to the cell region.

DESCRIPTION OF EMBODIMENTS

Next, embodiments will be described in detail with reference to the accompanying drawings.

Figure 1:
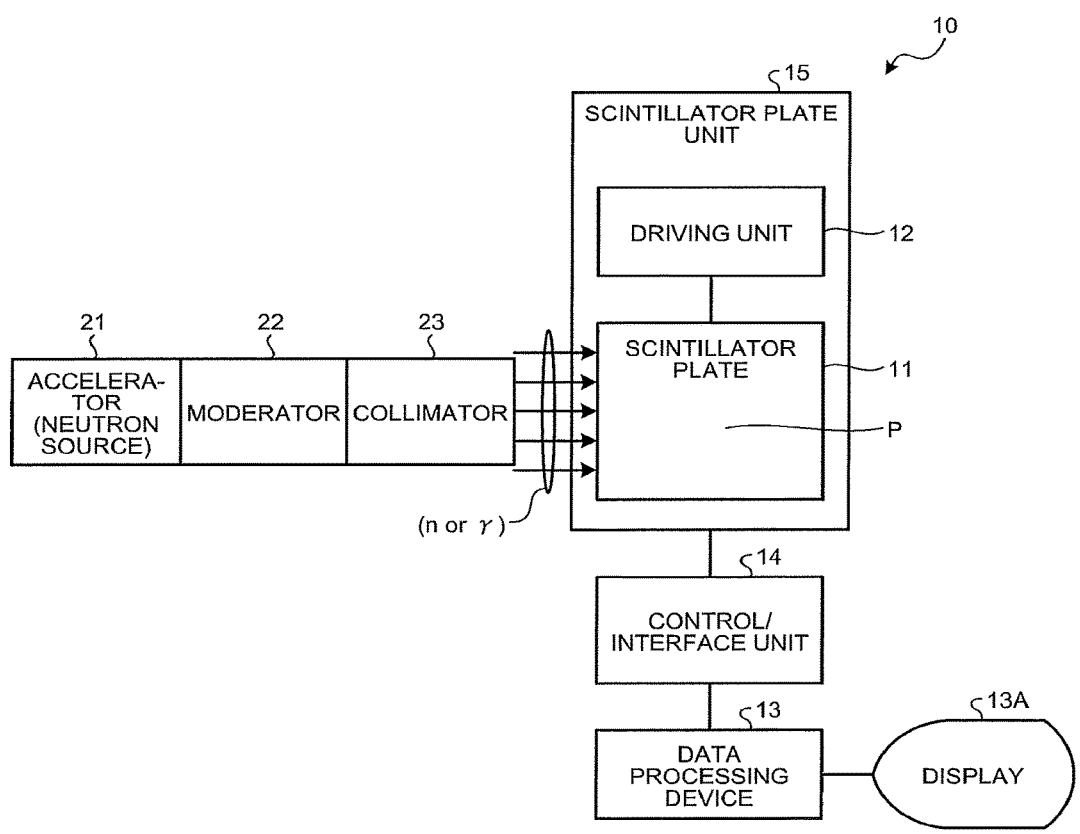
FIG. 1 is a view for explaining the outline configuration of a thermal neutron measurement system according to an embodiment.

FIG. 1 is a view for explaining the outline configuration of a thermal neutron measurement system according to an embodiment.

A thermal neutron measurement system 10 includes a scintillator plate 11, a driving unit 12, a data processing device 13, and a control/interface unit 14. The scintillator plate 11 has a detection face P on which a plurality of first cell regions CL1 (details thereof will be described later) capable of detecting incident thermal neutrons, fast neutrons, and gamma rays and a plurality of second cell regions CL2 (details thereof will be described later) capable of detecting fast neutrons and gamma rays and allowing the thermal neutrons to transmit therethrough are alternately arranged in a lattice form (two-dimensionally). The driving unit 12 drives the scintillator plate 11 in a plane containing the detection face P of the scintillator plate 11 to alternately switch the first cell regions CL1 and the second cell regions CL2 synchronously with a measurement with the scintillator plate 11. The data processing device 13 controls the driving unit 12 and calculates data on a thermal neutron flux based on detected data corresponding to detection signals of the scintillator plate 11. The control/interface unit 14 reads out the detected data from the scintillator plate 11 under the control of the data processing device 13 and performs interface with the data processing device 13.

In the above configuration, the scintillator plate 11 and the driving unit 12 form a scintillator plate unit 15.

A neutron source that generates the thermal neutrons to be incident on the scintillator plate 11 is, for example, an accelerator 21 that generates neutrons by accelerating protons to collide with a target, $^7$Li or $^9$Be for nuclear reaction. The neutrons emitted from the accelerator 21 are decelerated by a moderator (decelerator) 22, converted into collimated neutron beams by a collimator 23, and incident on the scintillator plate 11 for measuring the density of the incident thermal neutron beams. The thermal neutrons having transmitted through the scintillator plate 11 are emitted to an affected area of a patient for the purpose of treatment.

Next, the configuration of the scintillator plate in the embodiment will be described.

Figure 2:
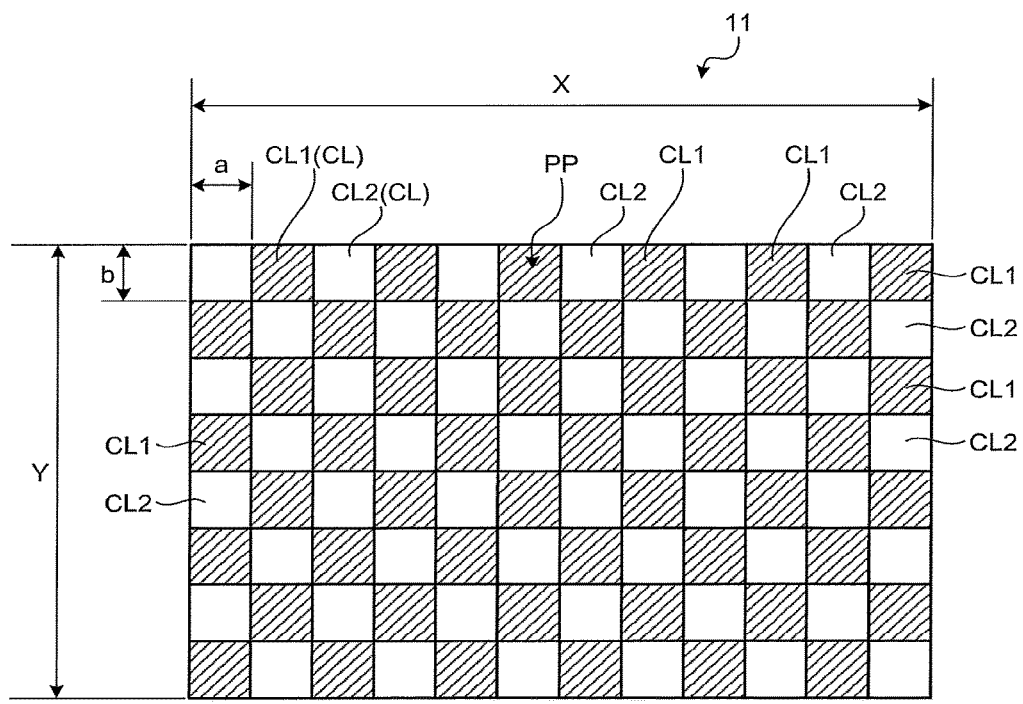
FIG. 2 is a plan view of the outline configuration of a scintillator plate in the embodiment.

FIG. 2 is a plan view of the outline configuration of the scintillator plate in the embodiment.

In the scintillator plate 11, the first cell regions CL1 and the second cell regions CL2 are discretely (dispersedly) arranged in the lattice (checkered) form, as illustrated in FIG. 2. The first cell regions CL1 and the second cell regions CL2 have the same dimensions and the shape of parallelogram (in FIG. 2, squares) when seen from the above. In the following description, the first cell regions CL1 and the second cell regions CL2 are collectively referred to as cell regions CL when they are not required to be distinguished.

Figure 3:
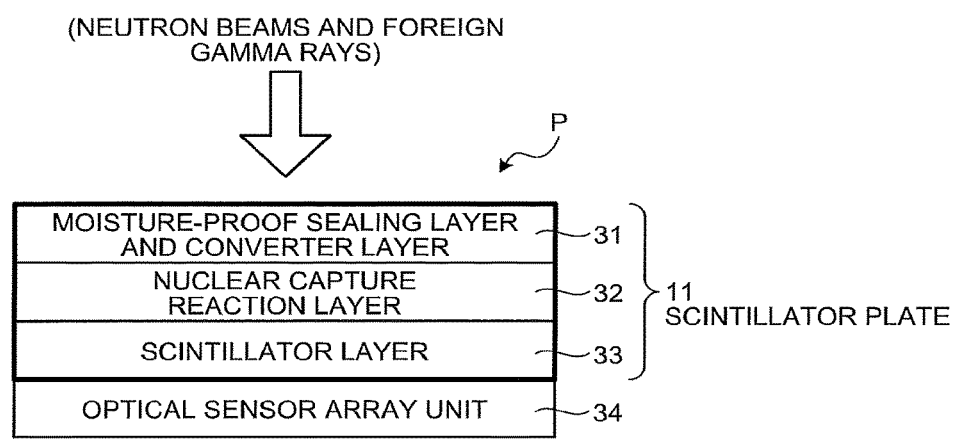
FIG. 3 is a sectional view of the outline configuration of the scintillator plate in the embodiment.

FIG. 3 is a sectional view of the outline configuration of the scintillator plate in the embodiment.

The scintillator plate 11 includes a moisture-proof sealing layer 31 and a nuclear capture reaction layer 32. The moisture-proof sealing layer 31 functions as a moisture-proof sealing member of the scintillator plate at the side of the detection face P on which the neutron beams and foreign gamma rays are incident, generates recoil protons from incident fast neutrons, and transmits epithermal neutrons therethrough. A nuclear capture reaction material (for example, LiF containing $^6$Li) is discretely arranged (for example, arranged in a lattice form) in the nuclear capture reaction layer 32.

The scintillator plate 11 further includes a scintillator layer 33 and an optical sensor array unit 34. The scintillator layer 33 receives helium atomic nuclei ($^4_2$He: α rays) and tritium ($^3$H) generated by nuclear capture reaction of the thermal neutrons incident on the nuclear capture reaction layer 32, foreign gamma rays, the recoil protons generated in the moisture-proof sealing layer 31, and converts their incident energy into light. The optical sensor array unit 34 receives the light converted by the scintillator layer 33 with arrayed optical sensors and outputs light reception signals corresponding to the respective cell regions CL to the control/interface unit 14.

Regions in which the moisture-proof sealing layer 31 and the nuclear capture reaction layer 32 are laminated on the scintillator layer 33 correspond to the first cell regions CL1 capable of detecting the thermal neutrons, part of the fast neutrons, and the gamma rays whereas regions in which the moisture-proof sealing layer 31 is laminated on the scintillator layer 33 correspond to the second cell regions CL2 capable of detecting part of the fast neutrons and the gamma rays.

For producing the nuclear capture reaction layer 32 of the scintillator plate 11, the nuclear capture reaction material is deposited by vacuum evaporation, dissolved in a solvent causing no decomposition reaction and applied, or powdered and adhered.

Next, a reason why LiF containing $^6$Li is used as the nuclear capture reaction material in the embodiment will be described.

Nuclear reaction using atomic nuclei of $^3$He, $^{10}$B, $^6$Li, $^{235}$U has been generally known for detecting neutrons.

To be specific, types of the nuclear reaction expressed by the following nuclear reaction equations (1) to (4) are exemplified.

$$^3\text{He}+n \rightarrow {}^3\text{H}+p+0.8 \text{ MeV} \quad (1)$$

[absorption cross-section of 5,328 barn]

$$^{10}\text{B}+n \rightarrow {}^7\text{Li}+{}^4\text{He}+2.3 \text{ MeV} \quad (2)$$

[absorption cross-section of 3,838 barn]

$$^6\text{Li}+n \rightarrow {}^4\text{He}+{}^3\text{H}+4.8 \text{ MeV} \quad (3)$$

[absorption cross-section of 940 barn]

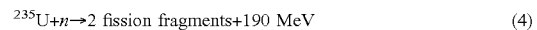
$$^{235}\text{U}+n \rightarrow 2 \text{ fission fragments}+190 \text{ MeV} \quad (4)$$

[absorption cross-section of 683 barn]

The atomic nuclei absorbing neutrons may release gamma rays (captured gamma rays), which will become unnecessary background noise for a neutrons detecting scintillator.

The nuclear reaction utilizing $^6$Li expressed by the equation (3), however, does not release gamma rays. The present embodiment thus employs the nuclear reaction utilizing $^6$Li expressed by the equation (3) and uses the LiF layer 32A as the nuclear capture reaction layer 32, aiming for reducing the background noise and achieving more accurate measurement. This should not, however, limit the nuclear capture reaction layer to the LiF layer and merely signifies that the nuclear capture reaction layer can be formed of a compound containing $^6$Li.

[1] First Embodiment

Next, the configuration of a scintillator plate according to a first embodiment as a specific example of the embodiment will be described.

Figure 4:
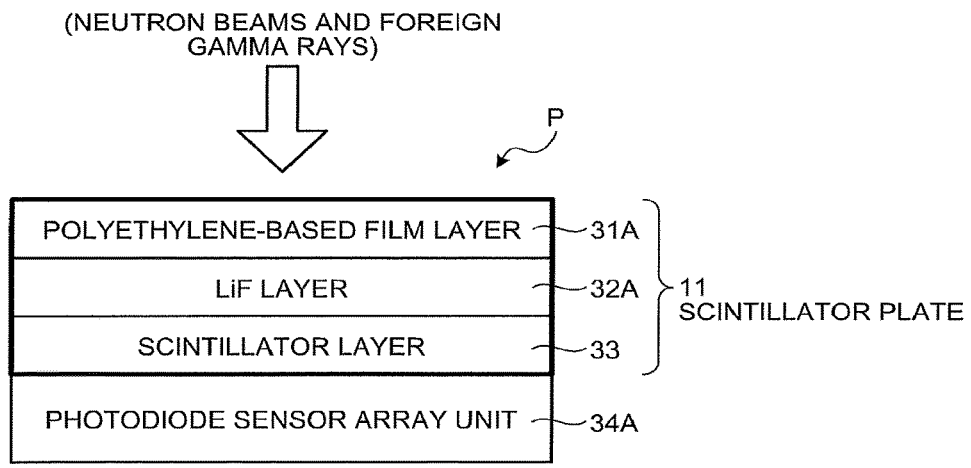
FIG. 4 is a sectional view of the outline configuration of a scintillator plate according to a first embodiment.

FIG. 4 is a sectional view of the outline configuration of the scintillator plate in the first embodiment.

The scintillator plate 11 includes a polyethylene-based film layer 31A, a LiF layer 32A, the scintillator layer 33, and a photodiode sensor array unit 34A. The polyethylene-based film layer 31A functions as the moisture-proof sealing layer 31 and contains a large number of hydrogen atoms. The LiF layer 32A functions as the nuclear capture reaction layer 32 and includes LiF discretely arranged in a lattice (checkered) form. The scintillator layer 33 receives helium atomic nuclei ($^4_2$He: α rays) and tritium ($^3$H) as charged particles generated by nuclear capture reaction of thermal neutrons incident on the LiF layer 32A, foreign gamma rays, recoil protons generated in the polyethylene-based film layer 31A, and converts their incident energy into light. The photodiode sensor array unit 34A functions as the optical sensor array unit 34.

Figure 5:
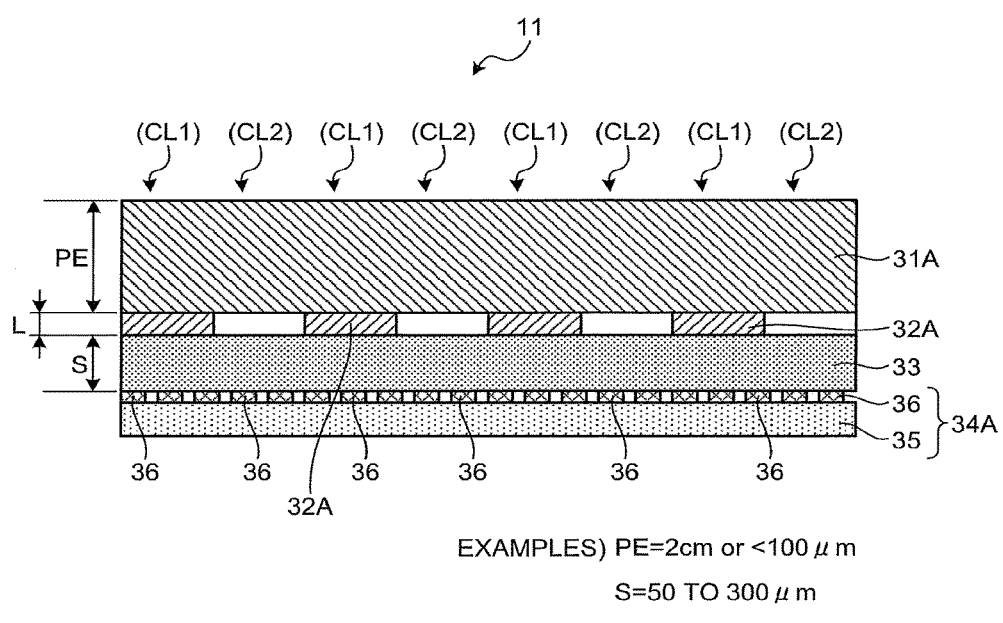
FIG. 5 is a sectional view of the detailed configuration of the scintillator plate in the first embodiment.

FIG. 5 is a sectional view of the detailed configuration of the scintillator plate in the first embodiment.

In FIG. 5, scales are not constant for the sake of simple understanding.

The photodiode sensor array unit 34A receives the light converted by the scintillator layer 33 with arrayed photodiodes (optical sensors) 36 on a glass substrate 35 and outputs light reception signals corresponding to the respective cell regions CL to the control/interface unit 14. A pitch of the photodiodes 36 is set to, for example, 140 μm and approximately 1,000 to 5,000 photodiodes 36 are arranged in each of the cell regions CL.

Figure 6:
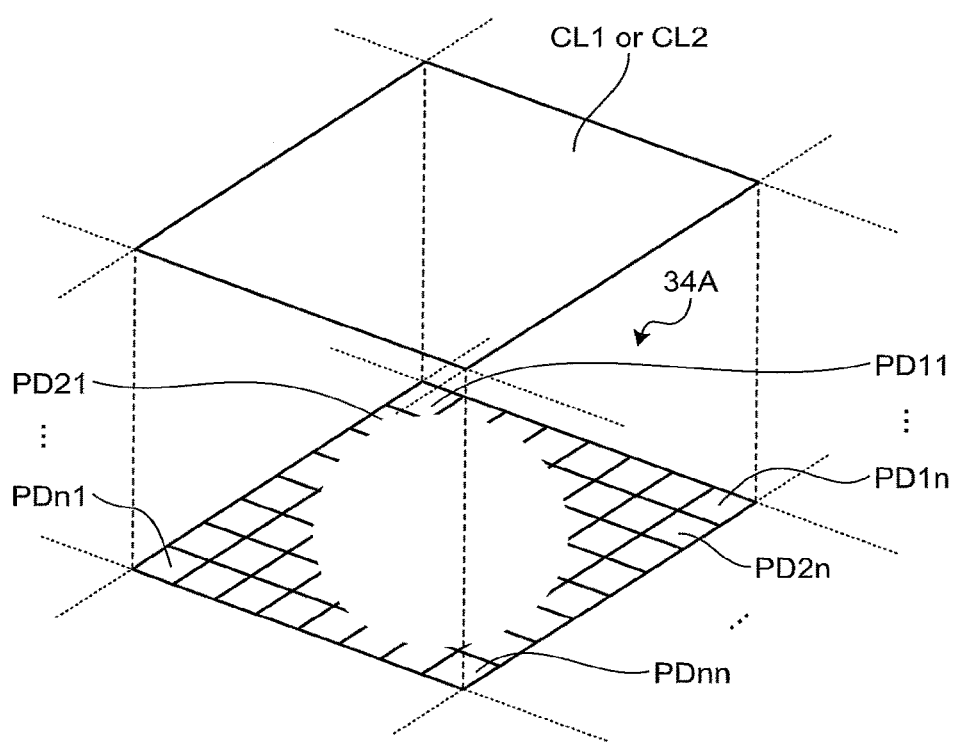
FIG. 6 is a view for explaining a relation between a cell region and photodiodes when arranged.

FIG. 6 is a view for explaining the relation between the cell region and the photodiodes when arranged.

In FIG. 6, the respective photodiodes 36 are denoted by PD11 to PDnn for identification.

As illustrated in FIG. 6, the photodiodes PD11 to PDnn or the photodiodes 36 are arranged in the photodiode sensor array unit 34A corresponding to the first cell regions CL1 or the second cell regions CL2, and the total number thereof is, for example, n×n.

The output of the scintillator plate 11 corresponding to the first cell regions CL1 or the second cell regions CL2 can be set to the sum or the average of outputs of the photodiodes PD11 to PDnn. Alternatively, among the photodiodes PD11 to PDnn, the output of the scintillator plate 11 can be set to the output of the photodiodes 36 representative of the first cell regions CL1 or the second cell regions CL2 or the sum or the average of outputs of a group of the photodiodes 36 representative of the first cell regions CL1 or the second cell regions CL2.

FIG. 7 is a view for explaining an example of output of the scintillator plate corresponding to the cell regions.

FIG. 8 is a view for explaining another example of the output of the scintillator plate corresponding to the cell regions.

FIG. 7 shows the example that the output of the first cell regions CL1 or the second cell regions CL2 is represented by the output of a photodiode PDx of the photodiodes PD11 to PDnn. FIG. 8 shows the example that the output of the first cell regions CL1 or the second cell regions CL2 is represented by the sum or the average value of outputs of a group PDG of four photodiodes 36.

Although in the above description the output(s) of one or four photodiode(s) 36 represents/represent the output of the first cell regions CL1 or the second cell regions CL2, it can be appropriately set in accordance with the processing capacity of the scintillator plate, the control/interface unit 14, or the data processing device 13.

The thickness PE of the polyethylene-based film layer 31A of the scintillator plate 11 in the first embodiment is set to smaller than 100 μm.

This is because with such a thickness PE, the polyethylene-based film layer 31A can provide a sufficient moisture-proof effect and allows most of fast neutrons and epithermal neutrons to pass therethrough except for part of the fast neutrons flicking out hydrogen atomic nuclei (recoil protons) of the polyethylene-based film layer 31A, so as to prevent attenuation and scattering of the thermal neutrons therein.

That is, the thermal neutrons attenuate and scatter in the polyethylene-based film layer 31A having a too large thickness PE, and thus cannot reach the subsequent LiF layer 32A with accurate intensity and positional information. The thickness PE of the polyethylene-based film layer 31A can be hence set to, for example, 25 to 50 μm in order to detect the thermal neutrons accurately. In this case, most of the fast neutrons and the epithermal neutrons pass through the polyethylene-based film layer 31A.

The thickness L of the vapor-deposited or applied LiF portions of the LiF layer 32A is set to approximately 10 μm.

Regarding the thickness L, $^6$Li forming the LiF layer 32A and the thermal neutrons yield nuclear capture reaction to generate α rays (He atomic nuclei) and tritium (tritium nuclei) and these charged particles are incident on the scintillator to emit light. The ranges of the generated He atomic nuclei and tritium nuclei are approximately 10 μm and approximately 50 μm, respectively. In view of this, the thickness L is set to 10 μm by way of example to ensure that the generated particles can be incident on the scintillator layer 33. The thickness L can be set to 10 to 50 μm.

Furthermore, the thickness S of the scintillator layer 33 is set to 50 to 300 μm in case of using, for example, CsI (Tl) as a material of the scintillator. The value of the thickness S is set to attain sufficient light emission and is obtained experientially. Along with an increase in the thickness S, the quantity of light emission tends to be saturated. Too large thickness is therefore meaningless and simply disadvantageous in terms of cost. The thickness S of the scintillator layer 33 is thus appropriately set. As long as the light emission with the secondary charged particles is ensured, smaller thickness S is more desirable because influence of unnecessary foreign gamma rays on the luminance of emitted light can be minimized by lowering the sensitivity to the gamma rays. The thickness S is set to, for example, 50 μm to 100 μm.

Next, operations in the first embodiment will be described.

Figure 9:
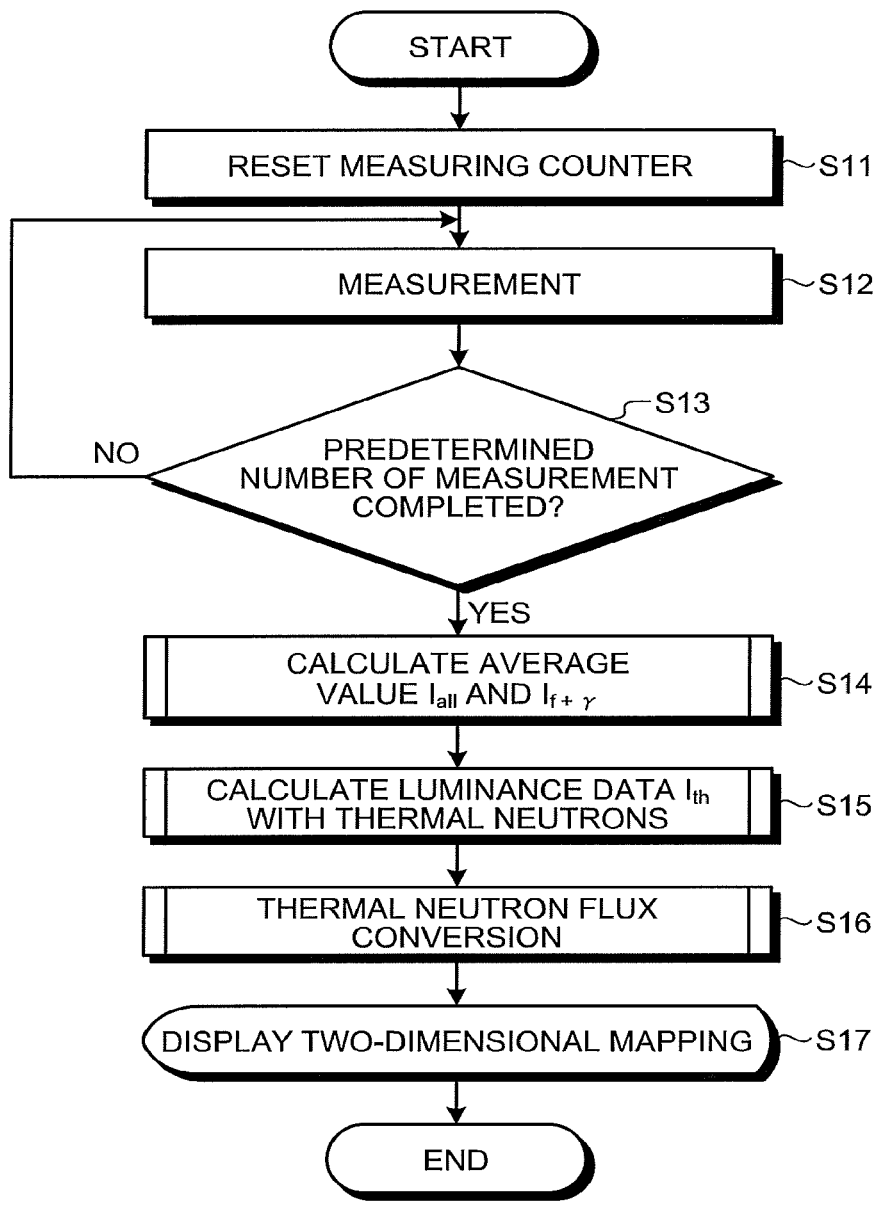
FIG. 9 is a processing flowchart of thermal neutron detection in the embodiment.

FIG. 9 is a processing flowchart of thermal neutron detection in the embodiment.

When receiving an instruction for detection of thermal neutrons from the data processing device 13, the control/interface unit 14 resets a measuring counter (step S11).

The measuring counter is used for counting the number of measurements of luminance values (sensors' sensing values) of the first cell regions CL1 and the second cell regions CL2 in order to reduce temporal fluctuation in the luminance values. When a length of time for which the luminance values of the first cell regions CL1 and the second cell regions CL2 are measured is appropriately set in a range of 1 ms to 1 sec and the values are measured five times, for example, an initial value is set to 5.

Figure 10:
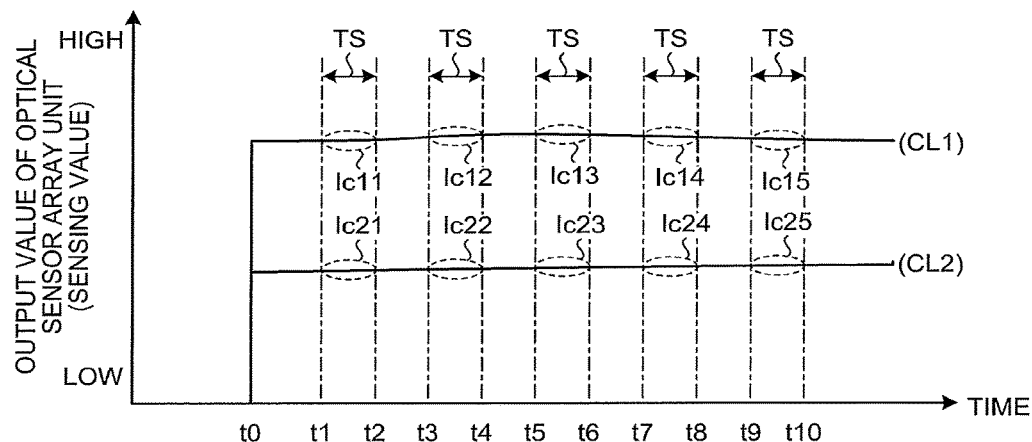
FIG. 10 is a view for explaining measurement processing.

FIG. 10 is a view for explaining measurement processing.

The control/interface unit 14 then measures the luminance values (step S12). The control/interface unit 14 subtracts 1 from a value of the measuring counter.

To be more specific, when neutron irradiation is started at time t0, the control/interface unit 14 acquires individual cumulative light quantities of the first cell regions CL1 and the second cell regions CL2 in a period from time t1 to time t2 until a predetermined measuring time elapses.

The predetermined measuring time is properly set to maintain the linearity of the acquired luminance values of the photodiodes without saturation (for example, 1 ms to 1 sec).

Subjects to be incident and behaviors thereof will be described for the first cell regions CL1 and the second cell regions CL2 separately.

First, the first cell regions CL1 are described.

The thermal neutron beams incident on the first cell regions CL1 transmit through the polyethylene-based film layer 31A having the small absorption cross-section relative to the thermal neutron beams, and reach the LiF layer 32A. The thermal neutron beams yield the nuclear capture reaction therein to generate helium atomic nuclei ($^4_2$He: α rays) and tritium ($^3$H) as the charged particles.

The generated helium atomic nuclei and tritium emit light in the scintillator layer 33 and the photodiode sensor array unit 34A receives and detects the light.

The epithermal neutron beams incident on the first cell regions CL1 pass through the polyethylene-based film layer 31A as they are due to the small thickness of the polyethylene-based film layer 31A, and transmit through the LiF layer 32A and the scintillator layer 33 as they are.

Part of the fast neutron beams incident on the first cell regions CL1 flick out the hydrogen atomic nuclei (recoil protons) of the polyethylene-based film layer 31A. The flicked recoil protons transmit through the LiF layer 32A and emit light in the scintillator layer 33. Then, the photodiode sensor array unit 34A receives and detects the light. Most of the fast neutrons however pass through the polyethylene-based film layer 31A as they are because of the thin thickness thereof.

The gamma rays incident on the first cell regions CL1 transmit through the polyethylene-based film layer 31A and the LiF layer 32A and emit light in the scintillator layer 33. Then, the photodiode sensor array unit 34A receives and detects the light.

Next, the second cell regions CL2 are described.

The thermal neutron beams incident on the second cell regions CL2 transmit through the polyethylene-based film layer 31A having the small absorption cross-section relative to the thermal neutron beams and transmit through the scintillator layer 33 without emitting light. The photodiode sensor array unit 34A does not thus detect light.

The epithermal neutron beams incident on the second cell regions CL2 pass through the polyethylene-based film layer 31A as they are because of the thin thickness, and transmit through the scintillator layer 33 without emitting light. Thus, the photodiode sensor array unit 34A does not detect light.

Part of the fast neutron beams incident on the second cell regions CL2 flick out the hydrogen atomic nuclei (recoil protons) of the polyethylene-based film layer 31A as with the fast neutron beams incident on the first cell regions CL1. The flicked recoil protons emit light in the scintillator layer 33. Then, the photodiode sensor array unit 34A receives and detects the light. Most of the fast neutrons however pass through the polyethylene-based film layer 31A having the thin thickness as they are.

The gamma rays incident on the second cell regions CL2 transmit through the polyethylene-based film layer 31A and emit light in the scintillator layer 33 as with the gamma rays incident on the first cell regions CL1. Then, the photodiode sensor array unit 34A receives and detects the light.

As a result of these, the thermal neutrons, part of the fast neutrons, and the gamma rays incident on the first cell regions CL1 are detectable whereas part of the fast neutrons and the gamma rays incident on the second cell regions CL2 are detectable.

At the time of the above-measurement, the driving unit 12 drives the scintillator plate 11 in a plane containing the detection face P of the scintillator plate 11, to alternately switch the first cell regions CL1 and the second cell regions CL2 synchronously with the measurement with the scintillator plate 11. It should be noted that a driving cycle may be longer than a measuring cycle as long as a neutron beam dose is temporally stable.

This makes it possible to effectively obtain a result of the detection from the first cell regions CL1 provided on the entire detection face P of the scintillator plate 11 and a result of the detection from the second cell regions CL2 provided on the entire detection face P of the scintillator plate 11, thereby detecting the intensity of the thermal neutron flux on any region of the detection face P of the scintillator plate 11.

Then, the control/interface unit 14 determines whether or not the predetermined number of measurements has been completed based on the measuring counter (step S13).

In the above example, upon completion of a single measurement, the measuring counter indicates the value "4" obtained by subtracting 1 from the initial value of 5. That is, the predetermined number of measurements has not been completed (the value of the measuring counter is not 0) (No at step S13). The process thus returns to step S12 for remeasurement.

When the value of the measuring counter is 0 in the determination at step S13, the control/interface unit 14 determines completion of the predetermined number of measurements (Yes at step S13) and proceeds to step S14.

At this point, as illustrated in FIG. 10, the control/interface unit 14 acquires data of five measurements in total, that is, measured data Ic11 and Ic21 corresponding to a sampling period TS from time t1 to time t2, measured data Ic12 and Ic22 corresponding to the sampling period TS from time t3 to time t4, measured data Ic13 and Ic23 corresponding to the sampling period TS from time t5 to time t6, measured data Ic14 and Ic24 corresponding to the sampling period TS from time t7 to time t8, and measured data Ic15 and Ic25 corresponding to the sampling period TS from time t9 to time t10. The measured data Ic11 to Ic15 represents luminance data in each first cell region CL1 of the entire detection face P and the measured data Ic21 to Ic25 represent luminance data in each second cell region CL2 of the entire detection face P.

The control/interface unit 14 transfers the measured data of the five measurements to a data processing device 13 in order.

Thereby, the data processing device 13 calculates an average value $T_{all}$ of the measured data of the five measurements in each of the present first cell regions CL1 and an average value $I_{f+\gamma}$ of the measured data of the five measurements in each of the present second cell regions CL2 by the following equations (step S14).

$$I_{all}=(Ic11+Ic12+Ic13+Ic14+Ic15)/5$$

$$I_{f+\gamma}=(Ic21+Ic22+Ic23+Ic24+Ic25)/5$$

In case that real-time property (immediacy) of the measurement matters, the initial value of the measuring counter may be set to one to perform only a single measurement without the averaging.

In this case, the average value $I_{all}$ of the measured data of the five measurements in the first cell regions CL1 corresponds to a measured value of all of the thermal neutrons, part of the fast neutrons, and the gamma rays that have been incident on each measure point of the detection face P of the scintillator in the measurement period. The average value $I_{f+\gamma}$ of the measured data of the five measurements in the second cell regions CL2 corresponds to a measured value from part of all the fast neutrons and the gamma rays that have been incident on measure points of the detection face P of the scintillator in the measurement period.

The data processing device 13 calculates luminance data $I_{th}$, which corresponds to a substantial measured value (NET value) of the thermal neutrons, at each measure point on the detection face P of the scintillator by the following equation (step S15).

$$I_{th}=I_{all}-I_{f+\gamma}$$

Figure 11:
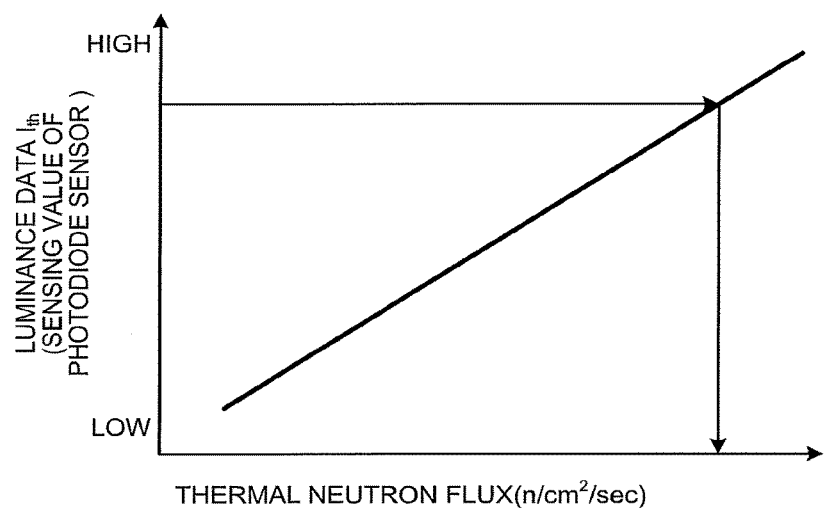
FIG. 11 is a conceptual view of a luminance data-thermal neutron flux conversion table.

FIG. 11 is a conceptual view of a luminance data-thermal neutron flux conversion table.

The data processing device 13 converts a thermal neutron flux to calculate the intensity of the thermal neutron flux with reference to a pre-stored luminance data $I_{th}$ to thermal neutron flux conversion table the concept of which is illustrated in FIG. 11 (or using a conversion function) (step S16).

Then, the data processing device 13 displays, on the screen of a display 13A, a two-dimensional mapping that two-dimensionally displays the intensities of the thermal neutron flux associated with the respective cell regions CL (step S17).

The two-dimensional mapping display is intended for medical use such as radiotherapy with neutron beams, to develop, by simulation, a treatment plan including the optimal values of necessary neutron flux intensity for a site of a patient or a focus depending on the patient or species of the focus. Quality assurance (QA) in radiation is practiced for checking actual neutron flux intensities before the treatment. For QA in radiation, the two-dimensional mapping display is used for calculating and checking the actual neutron flux intensities on a two-dimensional plane in real time. The two-dimensional mapping display is also used for radiotherapy using the thermal neutron beams that pass through the second cell regions CL2, to be able to calculate and check the actual thermal neutron flux intensities on the two-dimensional plane in real time.

In this case, the two-dimensional mapping can be displayed such that a predetermined display region of the screen of the display 13A is divided in lattice to display the intensity values of the thermal neutron flux with numeric characters or by color coding on the respective divided regions.

It should be noted that instead of the two-dimensional mapping display, three-dimensional mapping display is feasible which expresses the intensity values of the thermal neutron flux by height.

As described above, the first embodiment can accurately measure the irradiance of the thermal neutron beams (intensity values of the thermal neutron flux) over the entire two-dimensional targeted detection region in real time over time.

[2] Second Embodiment

Next, the configuration of a scintillator plate according to a second embodiment will be described.

The first embodiment has described the first cell regions CL1 in which LiF is deposited by vacuum evaporation, applied, or adhered onto the top surface of the scintillator layer 33 and the polyethylene-based film layer 31A is laminated thereon as well as the second cell regions CL2 in which the polyethylene-based film layer 31A is directly laminated on the top surface of the scintillator layer 33. The second embodiment is different from the first embodiment in that the first cell regions CL1 are formed by mixing LiF powder into a scintillator powder material and filling grid frames with the mixture and the second cell regions CL2 are formed by filling the grid frames with the scintillator powder material.

Figure 12:
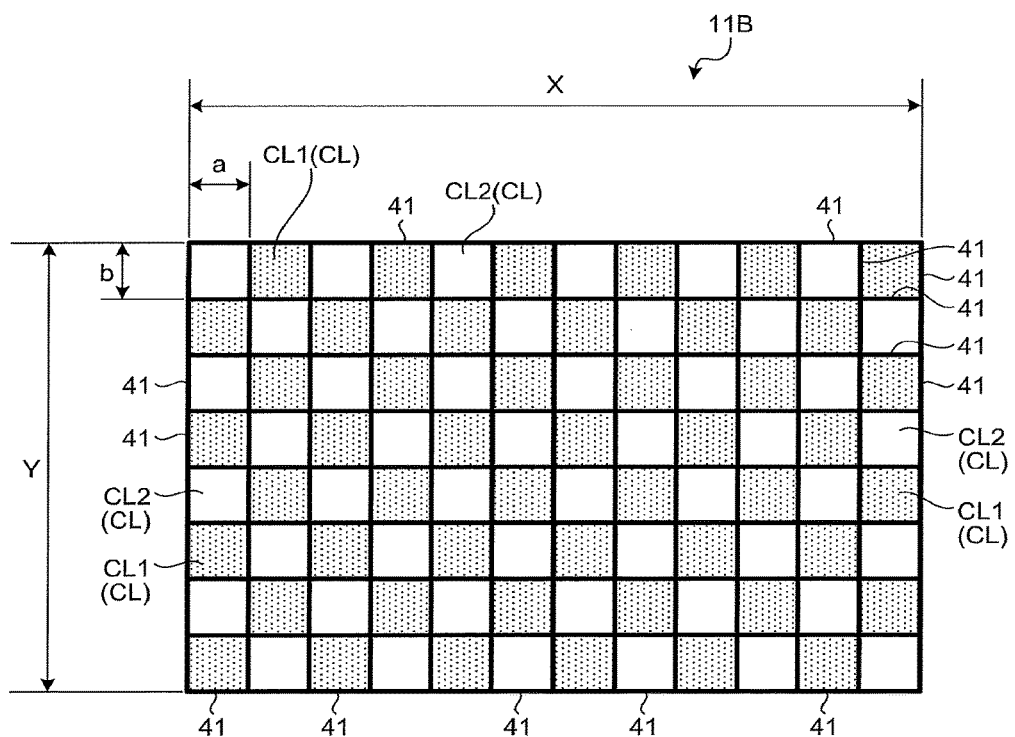
FIG. 12 is a plan view of the outline configuration of a scintillator plate according to a second embodiment.

FIG. 12 is a plan view of the outline configuration of the scintillator plate in the second embodiment.

In a scintillator plate 11B, the first cell regions CL1 and the second cell regions CL2 are partitioned by grid frames 41 and are discretely (dispersedly) arranged in a lattice (checkered) form, as illustrated in FIG. 12. Also in this case, the first cell regions CL1 and the second cell regions CL2 have the same dimensions when seen from above as in the first embodiment.

Figure 13:
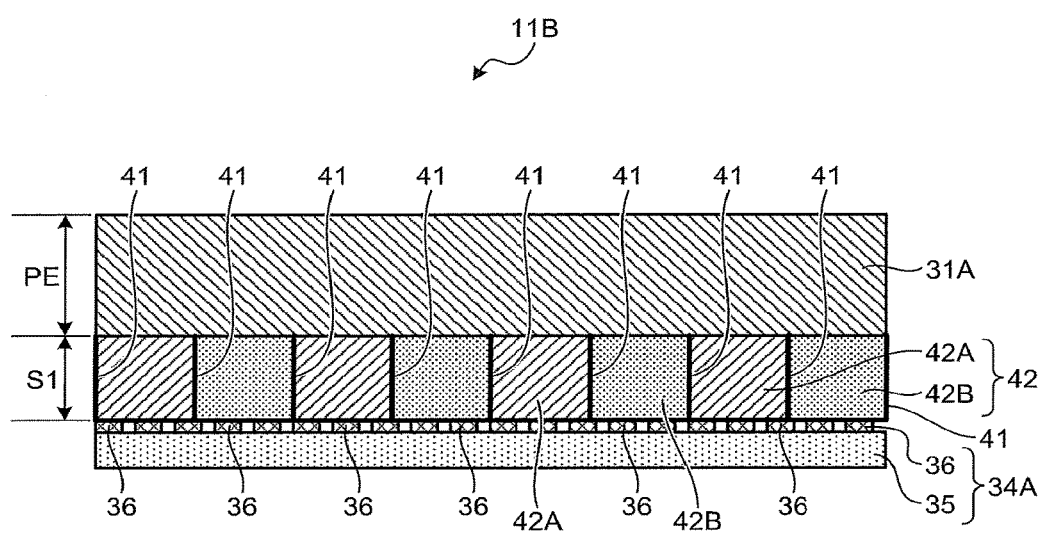
FIG. 13 is a sectional view of the outline configuration of the scintillator plate in the second embodiment.

FIG. 13 is a sectional view of the outline configuration of the scintillator plate in the second embodiment.

In FIG. 13, the same or like elements as those in FIG. 5 are denoted by the same reference numerals.

The scintillator plate 11B includes the polyethylene-based film layer 31A and a scintillator layer 42. The polyethylene-based film layer 31A functions as the moisture-proof sealing layer 31, generates recoil protons upon receiving incident fast neutrons from the detection face P on which neutron beams and foreign gamma rays are incident, and transmits epithermal neutrons therethrough. The scintillator layer 42 includes nuclear capture reaction/scintillator regions 42A filled with the mixture of the LiF powder and the scintillator powder and scintillator regions 42B filled with the scintillator powder. Both of the regions are partitioned by the grid frames 41 and discretely (dispersedly) arranged alternately in the lattice (checkered) form.

The thickness PE of the polyethylene-based film layer 31A of the scintillator plate 11B in the second embodiment is set to smaller than 100 μm for the same reason as that in the first embodiment.

The thickness S1 of the scintillator layer 42 is set to 50 to 300 μm in case of using, for example, CsI (Tl) as a material of the scintillator. The value of the thickness S1 is set to attain sufficient light emission and is obtained experientially. As in the first embodiment, too large thickness S1 tends to cause saturation of the quantity of light emission and is therefore meaningless and simply disadvantageous in terms of cost. The thickness S1 is thus appropriately set. As long as the light emission with the secondary charged particles is ensured, smaller thickness S1 is more desirable because influence of unnecessary foreign gamma rays on the luminance of emitted light can be minimized by lowering the sensitivity to the gamma rays. The thickness S1 is set to, for example, 50 μm to 100 μm.

Next, operations in the second embodiment will be described with reference to FIG. 13 and FIG. 9 again.

Upon receiving an instruction to detect the thermal neutrons from the data processing device 13, the control/interface unit 14 resets the measuring counter (step S11).

The control/interface unit 14 then starts measuring (step S12). Then, the control/interface unit 14 subtracts 1 from a value of the measuring counter.

Subjects to be incident and behaviors thereof will be described for the first cell regions CL1 and the second cell regions CL2 separately.

First, the first cell regions CL1 are described.

The thermal neutron beams incident on the first cell regions CL1 transmit through the polyethylene-based film layer 31A having a small absorption cross-section relative to the thermal neutron beams and reach the nuclear capture reaction/scintillator regions 42A. The thermal neutron beams yield nuclear capture reaction to generate helium atomic nuclei ($^4_2$He: α rays) and tritium ($^3$H) as charged particles and emit light. The photodiode sensor array unit 34A receives and detects the light.

The epithermal neutron beams incident on the first cell regions CL1 pass through the polyethylene-based film layer 31A having the thin thickness as they are, and transmit through the nuclear capture reaction/scintillator regions 42A as they are.

Part of the fast neutron beams incident on the first cell regions CL1 flick out hydrogen atomic nuclei (recoil protons) of the polyethylene-based film layer 31A. The flicked recoil protons emit light in the nuclear capture reaction/scintillator regions 42A. Then, the photodiode sensor array unit 34A receives and detects the light. Most of the fast neutrons however pass through the thin polyethylene-based film layer 31A as they are.

The gamma rays incident on the first cell regions CL1 emit light in the nuclear capture reaction/scintillator regions 42A. Then, the photodiode sensor array unit 34A receives and detects the light.

Next, the second cell regions CL2 are described.

The thermal neutron beams incident on the second cell regions CL2 transmit through the polyethylene-based film layer 31A having the small absorption cross-section relative to the thermal neutron beams and transmit through the scintillator regions 42B without emitting light. Thus, the photodiode sensor array unit 34A does not detect light.

The epithermal neutron beams incident on the second cell regions CL2 pass through the thin polyethylene-based film layer 31A as they are and transmit through the scintillator regions 42B without emitting light. Thus, the photodiode sensor array unit 34A does not detect light.

Part of the fast neutron beams incident on the second cell regions CL2 flick out the hydrogen atomic nuclei (recoil protons) of the polyethylene-based film 31A as with the fast neutron beams incident on the first cell regions CL1. The flicked recoil protons emit light in the scintillator regions 42B. Then, the photodiode sensor array unit 34A receives and detects the light. Most of the fast neutrons however pass through the thin polyethylene-based film layer 31A as they are.

The gamma rays incident on the second cell regions CL2 transmit through the polyethylene-based film layer 31A and emit light in the scintillator regions 42B in the same manner as the gamma rays incident on the first cell regions CL1. Then, the photodiode sensor array unit 34A receives and detects the light.

As a result of these, the thermal neutrons, part of the fast neutrons, and the gamma rays incident on the first cell regions CL1 are detectable whereas part of the fast neutrons and the gamma rays incident on the second cell regions CL2 are detectable.

The rest of the operations are the same as those in the first embodiment.

[2.1] Modification of Second Embodiment

Next, a modification of the second embodiment will be described.

Figure 14:
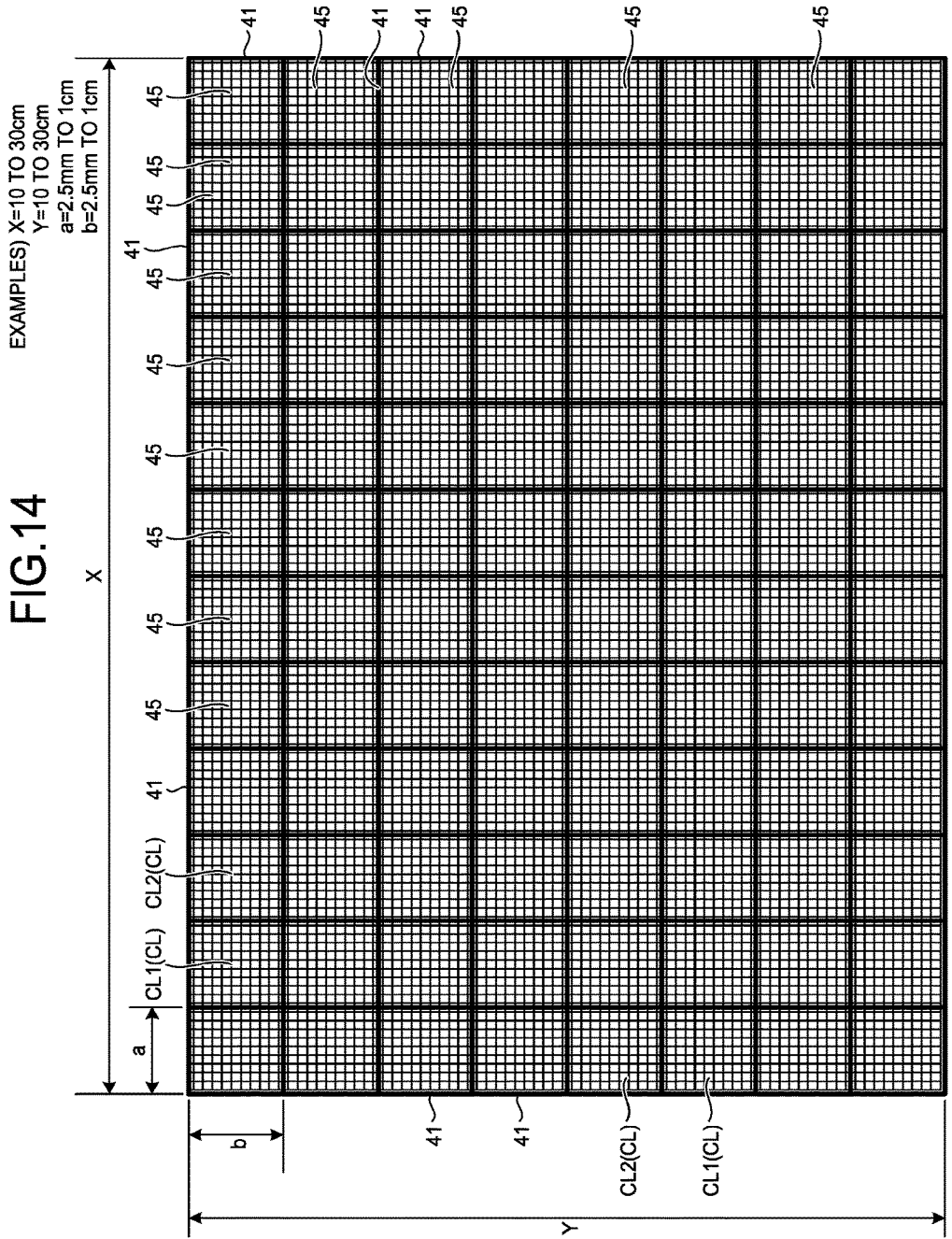
FIG. 14 is a sectional view of the outline configuration of a scintillator plate according to a modification of the second embodiment.

FIG. 14 is a sectional view of the outline configuration of a scintillator plate according to the modification of the second embodiment.

In the second embodiment, the first cell regions CL1 and the second cell regions CL2 have the same dimensions and correspond to the grid frames 41 on a one-to-one basis when seen from above. The modification of the second embodiment is different from the second embodiment in that as illustrated in FIG. 14, the first cell regions CL1 and the second cell regions CL2 are more finitely partitioned by grid frames 45 indicated by thin solid lines in FIG. 14. In FIG. 14, the bold solid lines 41 indicate boundaries between the first cell regions CL1 and the second cell regions CL2.

Thereby, the first cell regions CL1 and the second cell regions CL2 can be evenly filled with the LiF powder and the scintillator powder forming the nuclear capture reaction/scintillator regions 42A and the scintillator powder forming the scintillator regions 42B, respectively, enabling further stable measurements.

The pitch of the grid frames 45 is set to match, for example, the pitch (for example, 140 μm×140 μm) of the photodiodes of the photodiode sensor array unit 34A. The pitch of the grid frames 45 should not be limited to this example and can be appropriately set as long as it is smaller than, for example, the pitch of the first cell regions CL1 and the second cell regions CL2, 1 cm (=a)×1 cm (=b) and is the integral multiple of the pitch of the photodiodes, the first cell regions CL1 and the second cell regions CL2 include the same number of the grids, and the aperture ratio of each cell region L is not too low.

As described above, the second embodiment (including the modification) can accurately measure the irradiance of the thermal neutron beams (intensity values of the thermal neutron flux) over the entire target detection region as the first embodiment.

[3] Third Embodiment

The moisture-proof sealing layer 31 is formed of the polyethylene-based film in each of the above embodiments. A third embodiment will describe the example that, to have a moisture-proof function, the moisture-proof sealing layer 31 is made from a material containing no hydrogen atomic nucleus, that is, generating no recoil proton from incident fast neutrons, for example, an Al thin film (<50 μm).

[3.1] First Aspect

Figure 15:
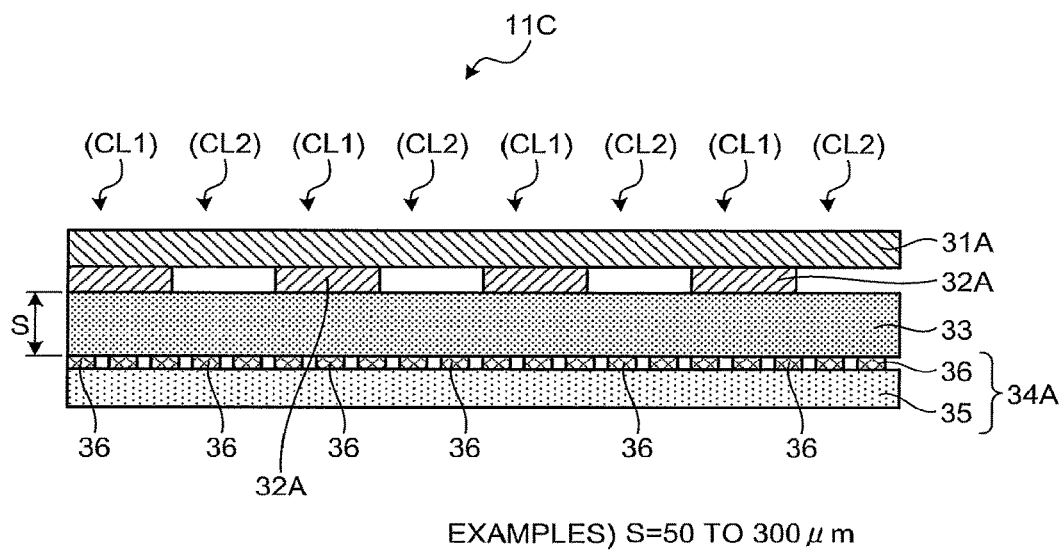
FIG. 15 is a sectional view of the outline configuration of a scintillator plate according to a first aspect of a third embodiment.

FIG. 15 is a sectional view of the outline configuration of a scintillator plate according to a first aspect of the third embodiment.

In FIG. 15, the same or like elements as those in FIG. 5 are denoted by the same reference numerals.

A scintillator plate 11C includes an Al thin-film layer 31A, the LiF layer 32A, the scintillator layer 33, and the photodiode sensor array unit 34A. The Al thin-film layer 31A functions same as the moisture-proof sealing layer 31 and transmits neutron beams and gamma rays therethrough. The LiF layer 32A functions as the nuclear capture reaction layer 32 and includes LiF discretely arranged in a lattice (checkered) form. The scintillator layer 33 converts, into light, foreign gamma rays and helium atomic nuclei ($^4_2$He:α rays) and tritium ($^3$H) as charged particles generated through the nuclear capture reaction of thermal neutrons incident on the LiF layer 32A. The photodiode sensor array unit 34A functions as the optical sensor array unit 34.

Subjects to be incident and behaviors thereof will be described for the first cell regions CL1 and the second cell regions CL2 separately.

First, the first cell regions CL1 are described.

The thermal neutron beams incident on the first cell regions CL1 yield the nuclear capture reaction in the LiF layer 32A to generate helium atomic nuclei ($^4_2$He: α rays) and tritium ($^3$H) as charged particles.

The generated helium atomic nuclei and tritium emit light in the scintillator layer 33 and the photodiode sensor array unit 34A receives and detects the light.

The epithermal neutron beams and the fast neutron beams incident on the first cell regions CL1 transmit through the LiF layer 32A and further transmit through the scintillator layer 33 without emitting light. Thus, the photodiode sensor array unit 34A does not detect light.

The gamma rays incident on the first cell region CL1 transmit through the LiF layer 32A and emit light in the scintillator layer 33. Then, the photodiode sensor array unit 34A receives and detects the light.

Next, the second cell regions CL2 are described.

The thermal neutron beams, the epithermal neutron beams, and the fast neutron beams incident on the second cell regions CL2 transmit through the scintillator layer 33 without emitting light. Hence, the photodiode sensor array unit 34A does not detect light.

The gamma rays incident on the second cell regions CL2 emit light in the scintillator layer 33 as with the gamma rays incident on the first cell regions CL1. Then, the photodiode sensor array unit 34A receives and detects the light.

As a result of these, the thermal neutrons and the gamma rays incident on the first cell regions CL1 can be detected whereas the gamma rays incident on the second cell regions CL2 can be detected.

By calculating the difference between them, thus, the intensity value of the neutron flux of the incident thermal neutrons can be obtained as in the first embodiment and the second embodiment.

The rest of the operations are the same as those in the first embodiment.

[3.2] Second Aspect

Figure 16:
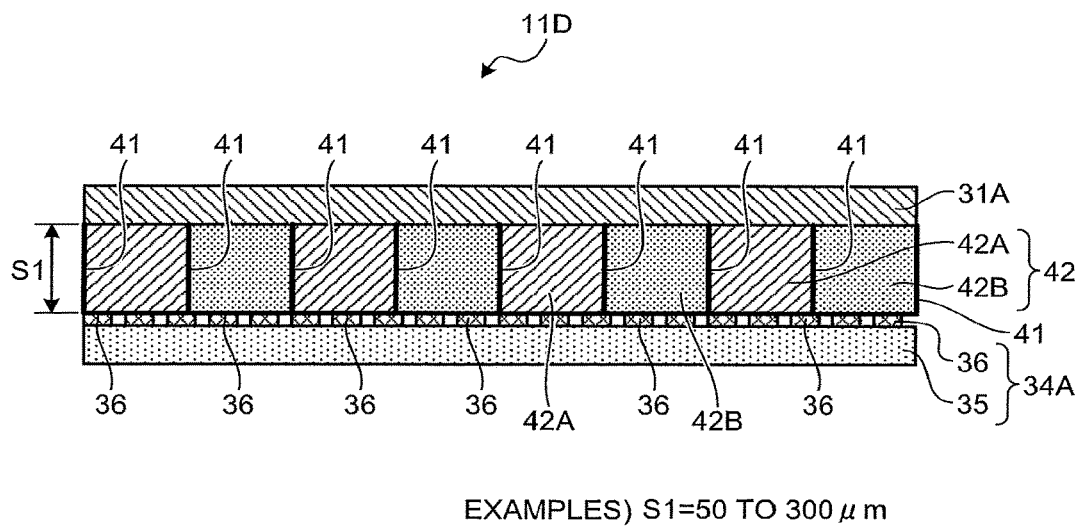
FIG. 16 is a sectional view of the outline configuration of a scintillator plate according to a second aspect of the third embodiment.

FIG. 16 is a sectional view of the outline configuration of a scintillator plate according to a second aspect of the third embodiment.

In FIG. 16, the same or like elements as those in FIG. 13 are denoted by the same reference numerals.

A scintillator plate 11D includes the scintillator layer 42 in which the nuclear capture reaction/scintillator regions 42A and the scintillator regions 42B are partitioned by the grid frames 41 and discretely arranged alternately (in checkered form). The nuclear capture reaction/scintillator regions 42A are filled with the mixture of the LiF powder and the scintillator powder and the scintillator regions 42B are filled with the scintillator powder.

In the above configuration, the thickness S1 of the scintillator layer 42 is set to 50 to 300 μm in case of using, for example, CsI (Tl) as a material of the scintillators. The value of the thickness S1 is set to attain sufficient light emission and is obtained experientially. Along with an increase in the thickness S1, the quantity of light emission tends to be saturated. Too large thickness is therefore meaningless and simply disadvantageous in terms of cost. The thickness S1 is thus appropriately set. As long as the light emission with the secondary charged particles is ensured, smaller thickness S1 is more desirable because influence of unnecessary foreign gamma rays on the luminance of light emission can be minimized by lowering the sensitivity to the gamma rays. The thickness S1 is set to, for example, 50 μm to 100 μm.

Subjects to be incident and behaviors thereof will be described for the first cell regions CL1 and the second cell regions CL2 separately.

First, the first cell regions CL1 are described.

The thermal neutron beams incident on the first cell regions CL1 reach the nuclear capture reaction/scintillator regions 42A and yield nuclear capture reaction to generate helium atomic nuclei ($^4_2$He: α rays) and tritium ($^3$H) as charged particles. The generated helium atomic nuclei and tritium emit light and the photodiode sensor array unit 34A receives and detects the light.

The epithermal neutron beams and the fast neutron beams incident on the first cell regions CL1 transmit through the nuclear capture reaction/scintillator regions 42A without emitting light. Thus, the photodiode sensor array unit 34A does not detect light.

The gamma rays incident on the first cell regions CL1 emit light in the nuclear capture reaction/scintillator regions 42A and the photodiode sensor array unit 34A receives and detects the light.

Next, the second cell regions CL2 are described.

The thermal neutron beams incident on the second cell regions CL2 transmit through the scintillator regions 42B without emitting light. Thus, the photodiode sensor array unit 34A does not detect light.

The epithermal neutron beams and the fast neutron beams incident on the second cell regions CL2 transmit through the scintillator regions 42B without emitting light. Thus, the photodiode sensor array unit 34A does not detect light.

The gamma rays incident on the second cell regions CL2 emit light in the scintillator regions 42B as with the gamma rays incident on the first cell regions CL1, and the photodiode sensor array unit 34A receives and detects the light.

As a result of these, the thermal neutrons and the gamma rays incident on the first cell regions CL1 can be detected whereas the gamma rays incident on the second cell regions CL2 can be detected.

By calculating a difference between them, hence, the intensity value of the neutron flux of the incident thermal neutrons can be obtained as in the first embodiment and the second embodiment.

The rest of the operations are the same as those in the first embodiment.

[4] Fourth Embodiment

An epithermal neutron beam detecting device which targets supplied epithermal neutron beams (epithermal neutron mode) can be attained by adhering a polyethylene-based layer made of the same material in thickness of approximately 2 cm onto the polyethylene-based film layer 31A functioning as the moisture-proof sealing layer 31 in the first embodiment and the second embodiment.

This is because the thickness PE of the polyethylene-based layer is set to a distance that allows the epithermal neutrons to collide with hydrogen atomic nuclei and turn into thermal neutrons and the thermal neutrons to reach the subsequent LiF layer 32A. In this case, part of the fast neutrons flick out the hydrogen atomic nuclei (recoil protons) of the polyethylene-based layer and emit light in the scintillator regions, and the gamma rays emit light in the scintillator regions as in the first embodiment and the second embodiment.

Meanwhile, the thermal neutrons further attenuate and scatter by collision with the hydrogen atomic nuclei in the thick polyethylene-based layer and reach the nuclear capture reaction portion (LiF portion) to cause background light emission. The luminance of the background light emission can be obtained by separately measuring only the thermal neutron beams in the thermal neutron mode in the fourth embodiment and subtracting the resultant from a net measured value of the thermal neutron beams obtained by actual measurement of the epithermal neutron beams.

Through the first cell regions CL1 detected are the incident background thermal neutrons occurring from the further attenuated and scattered thermal neutrons in the polyethylene-based layer, the thermal neutrons occurring from the decelerated epithermal neutrons in the polyethylene-based layer, part of the fast neutrons, and the gamma rays. Part of the fast neutrons and the gamma rays are detected through the second cell regions CL2. The rest of the operations are the same as those in the first embodiment and the second embodiment.

[5] Modification of Embodiments

In the above embodiments, the first cell regions CL1 and the second cell regions CL2 are discretely arranged in the lattice (checkered) form. Alternatively, the first cell regions CL1 and the second cell regions CL2 can be both arranged linearly and the linear first cell regions CL1 and the linear second cell regions CL2 can be alternately aligned in parallel in a striped form. In this case, the driving unit 12 may drive the scintillator unit in the direction orthogonal to (intersecting with) the line extending direction.

In the above, the same numbers (areas) of first cell regions CL1 and second cell regions CL2 having the same shape are described. Alternatively, the first cell regions CL1 and the second cell regions CL2 can be different in number and shape as long as the area ratio thereof is known in advance. In this case, however, calculation factors are increased from those in each of the above embodiments. For this reason, it is preferable that the numbers (areas) and shapes of first cell regions CL1 and second cell regions CL2 are the same in view of accuracy of the detection or simple processing.

Although some embodiments of the present invention have been described, these embodiments are merely examples and not intended to limit the scope of the invention. These novel embodiments can be implemented in various other modes and various omissions, replacements, and changes can be performed without departing from the gist of the invention. These embodiments and modifications thereof are encompassed in the gist and the scope of the invention and are also encompassed in the invention described in the claims and equivalents thereof.

The invention claimed is:

1. A thermal neutron detecting device comprising:
   a scintillator unit including:
      a scintillator layer that emits light upon receiving incident gamma ray or charged particles; and
      a nuclear capture reaction layer laminated on a side of the scintillator layer on which the gamma ray or the charged particles are incident, and including first cell regions and second cell regions two-dimensionally, dispersedly arranged along an incidence plane of the gamma ray or the charged particles, the first cell regions containing a $^6$Li compound as a nuclear capture reaction material that yields nuclear capture reaction with incident thermal neutrons to generate the charged particles, the second cell regions containing no nuclear capture reaction material; and
   an optical sensor array unit disposed at the scintillator layer side of the scintillator unit and is configured to detect a quantity of the emitted light in association with each of the first and second cell regions.

2. The thermal neutron detecting device according to claim 1, comprising
   a moisture-proof sealing layer laminated on an incidence side of the nuclear capture reaction layer, that functions as a moisture-proof sealing member and generates recoil protons as the charged particles upon receiving incident fast neutrons.

3. The thermal neutron detecting device according to claim 1, wherein the $^6$Li compound as the capture reaction material is LiF.

4. The thermal neutron detecting device according to claim 1, wherein the first cell regions and the second cell regions are dispersedly arranged in a lattice form.

5. The thermal neutron detecting device according to claim 1, wherein the first cell regions and the second cell regions are provided at a predetermined area ratio.

6. The thermal neutron detecting device according to claim 5, wherein the predetermined area ratio is one to one.

7. A thermal neutron detecting device comprising:
   a scintillator unit including a scintillator layer including first cell regions and second cell regions two-dimensionally, dispersedly arranged along an incidence plane of a gamma ray or thermal neutrons, the first cell regions containing a $^6$Li compound as a nuclear capture reaction material that yields nuclear capture reaction with incident thermal neutrons to generate charged particles, the second cell regions containing no nuclear capture reaction material;
   an optical sensor array unit disposed, facing the scintillator unit, and configured to detect a quantity of light emission in association with each of the first and second cell regions; and
   a moisture-proof sealing layer laminated on the side of the scintillator layer on which the gamma ray or the thermal neutrons are incident, to function as a moisture-proof sealing member and generate recoil protons as the charged particles upon receiving incident fast neutrons.

8. A scintillator unit comprising:
   a scintillator layer that emits light upon receiving incident gamma ray or charged particles; and
   a nuclear capture reaction layer laminated on a side of the scintillator layer on which the gamma ray or the charged particles are incident, and including first cell regions and second cell regions two-dimensionally, dispersedly arranged along an incidence plane of the gamma ray or the charged particles, the first cell regions containing a $^6$Li compound as a nuclear capture reaction material that yields nuclear capture reaction with incident thermal neutrons to generate the charged particles, the second cell regions containing no nuclear capture reaction material.

9. The scintillator unit according to claim 8, further comprising
   a moisture-proof sealing layer laminated on an incidence side of the nuclear capture reaction layer, to function as a moisture-proof sealing member and generate recoil protons as the charged particles upon receiving incident fast neutrons.

10. The scintillator unit according to claim 8, wherein the $^6$Li compound as the capture reaction material is LiF.

11. A thermal neutron detecting system comprising:
    a thermal neutron detecting device comprising
       a scintillator unit including
          a scintillator layer that emits light upon receiving incident gamma ray or charged particles, and
          a nuclear capture reaction layer laminated on a side of the scintillator layer on which the gamma ray or the charged particles are incident, and including first cell regions and second cell regions two-dimensionally, dispersedly arranged along an incidence plane of the gamma ray or the charged particles, the first cell regions containing a $^6$Li compound as a nuclear capture reaction material that yields nuclear capture reaction with incident thermal neutrons to generate the charged particles, the second cell regions containing no nuclear capture reaction material, and an optical sensor array unit disposed at the scintillator layer side of the scintillator unit, and configured to detect a quantity of the emitted light in association with each of the first and second cell regions; and a data processing device that calculates a thermal neutron flux based on a difference between the quantity of the emitted light corresponding to the first cell regions and the quantity of the emitted light corresponding to the second cell regions, on the basis of an output from the thermal neutron detecting device.

12. The thermal neutron detecting system according to claim 11, wherein the $^6$Li compound as the nuclear capture reaction material is LiF.

13. The thermal neutron detecting system according to claim 11, further comprising a driving unit that drives the scintillator unit along the incidence plane independently of the optical sensor array unit and synchronously with the detection such that light receiving positions on the optical sensor array unit from the first cell regions and from the second cell regions are alternately switched.

14. A thermal neutron detecting system comprising:

a thermal neutron detecting device comprising a scintillator unit including a scintillator layer including first cell regions and second cell regions two-dimensionally, dispersedly arranged along an incidence plane of gamma rays or thermal neutrons, the first cell regions containing a $^6$Li compound as a nuclear capture reaction material that yields nuclear capture reaction with incident thermal neutrons to generate charged particles, the second cell regions containing no nuclear capture reaction material, an optical sensor array unit disposed, facing the scintillator unit, and configured to detect a quantity of light emission in association with each of the first and second cell regions, and a moisture-proof sealing layer laminated on the side of the scintillator layer on which the gamma ray or the thermal neutrons are incident, to function as a moisture-proof sealing member and generate recoil protons as the charged particles upon receiving incident fast neutrons; and a data processing device that calculates a thermal neutron flux based on a difference between the quantity of light emission corresponding to the first cell regions and the quantity of light emission corresponding to the second cell regions, on the basis of an output from the thermal neutron detecting device.

* * * * *